United States Patent [19]

Sato et al.

[11] Patent Number: 4,514,229
[45] Date of Patent: Apr. 30, 1985

[54] PAPER SIZING COMPOSITION

[75] Inventors: Atsushi Sato, Tokyo; Yoshikazu Murai, Yokohama; Masahito Goto, Kawasaki; Kanji Mochizuki, Yokohama, all of Japan

[73] Assignee: Nippon Petrochemicals Company, Limited, Japan

[21] Appl. No.: 599,933

[22] Filed: Apr. 13, 1984

[30] Foreign Application Priority Data

Apr. 16, 1983 [JP]  Japan ................................. 58-67187

[51] Int. Cl.$^3$ .......................... C08K 5/15; C08K 5/48; D21D 3/00
[52] U.S. Cl. .................... 106/135; 106/213; 162/158; 524/112
[58] Field of Search ............. 106/213, 125, 135; 524/112; 162/158

[56] References Cited

U.S. PATENT DOCUMENTS 4,118,244 10/1978 Selwitz ................................. 106/270
4,207,142 6/1980 Shepherd ............................. 106/213
4,222,820 9/1980 Hiskens .............................. 106/213

*Primary Examiner*—Theodore Morris
*Attorney, Agent, or Firm*—Scully, Scott, Murphy & Presser

[57] ABSTRACT

An paper sizing composition which is suitable for use in neutral to alkaline paper making processes, which produces excellent sizing effect and which is well dispersed in water. Both the sizing effect and dispersion stability of the prepared sizing medium are durable. The paper sizing composition comprises: 20 to 90% by weight of (A) a reaction product and/or its hydrogenation product which reaction product is obtained by adding maleic anhydride to branched internal olefins having 14 to 36 carbon atoms which are obtained by oligomerizing one or a mixture of olefin starting materials having 6 to 18 carbon atoms and 10 to 80% by weight of (B) another reaction product and/or its hydrogenation product which reaction product is obtained by reacting maleic anhydride with straight chain internal olefins having 14 to 36 carbon atoms.

12 Claims, No Drawings

PAPER SIZING COMPOSITION

BACKGROUND OF THE INVENTION (1) Field of the Invention

This invention relates to a paper sizing composition for use in paper making. More particularly, the invention relates to a paper sizing composition which is employed in the range of neutral to alkali without using aluminum sulfate as fixing agent.

(2) Description of the Prior Art

In the paper manufacturing industry, sizing agents that are prepared from natural rosins or modified rosins, and especially, fortified rosin sizing agents that are prepared by saponifying maleic-modified rosins, are regarded as most preferable ones and they are widely used. These sizing agents are used together with aluminum sulfate and they are fixed to paper fibers under acidic conditions of pH 4.0 to 5.0. Owing to the acidic conditions in the use of these sizing agents, the following disadvantages are caused to occur. That is, paper making machinery suffers from corrosion, the strength and durability of obtained paper are lowered, and inexpensive alkaline fillers such as calcium carbonate cannot be used because the alkaline fillers are decomposed under the acidic condition. Therefore, it has been difficult to reduce much the production cost for paper making.

For this reason, neutral sizing agents which can be fixed to wood pulp without using aluminum sulfate, were looked for and some neutral sizing agents which give excellent sizing effect in the range of neutral to alkali have been proposed. For example, such a sizing agent is known that alkylketene dimer is dispersed in water in the presence of cationized starch. The sizing agent is, however, defective in that the cost is high and it takes much time to produce desired sizing effect.

Besides the above sizing agent, several neutral sizing agents of alkenyl succinic anhydride type have been proposed.

In British Pat. No. 2,015,612, there is proposed "substituted succinic anhydrides having substituent groups of butene oligomers having 16 to 40 carbon atoms". The compounds, however, are not satisfactory yet in sizing effect.

In U.S. Pat. No. 3,821,069 is disclosed a sizing agent which comprises the reaction product between maleic anhydride and internal olefins that are represented by the following general formula:

$$R_x-CH_2-CH=CH-CH_2-R_y$$

wherein $R_x$ and $R_y$ are, respectively, alkyl radicals containing 4 to 10 carbon atoms.

In Japanese Laid-Open Patent Publication No. 57-154,495 is proposed a reactive sizing agent which consists of "an alkenyl succinic anhydride mixture that is produced by adding maleic anhydride to a mixture of straight chain internal olefins which have 8 to 18 carbon atoms and double bonds of which are almost evenly distributed to every position except α-position. These sizing agents are high in reactivity with paper fiber, however, they do not produce sufficient sizing effect. In addition, they are liable to be hydrolyzed and they reduce its effect with the passage of time. Furthermore, when they are dispersed in water with a dispersing agent such as cationized starch, they sometimes become gel soon after the preparation. Even when the gel is diluted with water, homogeneous dispersion cannot be obtained, and if it is used as it stands, paper making machines are soiled as well as sufficient sizing effect cannot be attained, which facts will cause several troubles in paper making processes.

As described above, the known sizing agents are not satisfactory in view of sizing effect, dispersibility in water and/or stability of dispersion. Therefore, development of a more desirable neutral sizing agent is eagerly wanted.

BRIEF SUMMARY OF THE INVENTION

In view of the above circumstances, the inventors of the present application have carried out extensive investigations and experiments in order to develop a new sizing agent which is free from the above-described disadvantages. As a result, the inventors have found that the combination of specific sizing agents can simultaneously meet all the above requirements, thereby accomplishing the present invention.

It is, therefore, the primary object of the present invention to provide a novel and improved paper sizing composition that is free from the disadvantages which are caused to occur in the conventional art.

Another object of the present invention is to provide a paper sizing composition which produces excellent sizing effect and which is prepared without difficulty.

A further object of the invention is to provide a paper sizing composition which produces the sizing effect under neutral to alkaline conditions without using aluminum sulfate as fixing agent.

Still a further object of the present invention is to provide a paper sizing composition which can be dispersed well in water, which is compatible with various kinds of paper making additives and which can be preserved for a long time.

In accordance with the present invention, the paper sizing composition comprises:

20 to 90% by weight of (A) a reaction product and/or its hydrogenation product which reaction product is obtained by adding maleic anhydride to branched internal olefins having 14 to 36 carbon atoms which are obtained by oligomerizing one or a mixture of olefin starting materials having 6 to 18 carbon atoms and 10 to 80% by weight of (B) another reaction product and/or its hydrogenation product which reaction product is obtained by reacting maleic anhydride with straight chain internal olefins having 14 to 36 carbon atoms.

DETAILED DESCRIPTION OF THE INVENTION

The olefin starting materials used for preparing (A) component of the invention are any of those having 6 to 18 carbon atoms, preferably 8 to 12 carbon atoms, and are those which can be oligomerized.

When a reaction product prepared from olefin starting materials having less than 6 carbon atoms is used for paper sizing composition, the sizing effect is insufficient and dispersion stability is not good. On the other hand, when the olefin starting material of more than 18 carbon atoms is used, sizing effect is produced, however, the reaction product is inconvenient for practical uses because of its high viscosity.

Preferable olefin starting materials are exemplified by straight chain α-olefins such as octene-1, decene-1 and dodecene-1; straight chain internal olefins such as octene-2, octene-4, decene-3, decene-5, undecene-3, undecene-5, dodecene-4, dodecene-6, tetradecene-5 and tetradecene-7.

These olefins can be used either singly or in a mixture of two or more kinds. From economical viewpoint, mixtures of two or more kinds of olefins are preferably used. The branched internal olefin having 14 to 36 carbon atoms can be obtained by treating the above olefins under proper conditions in the presence of an oligomerization catalyst.

As the oligomerization catalysts, acid catalysts and organometallic complexes are used. Acid catalysts are exemplified by homogeneous or heterogeneous catalysts such as cation exchange resins having fluorosulfonic groups, fluoromethane sulfonic acid, $AlCl_3$-electron donor, $BF_3$-electron donor, mineral acids such as $H_2SO_4$, acid clay minerals such as acid clay and activated clay, synthetic silica alumina and heteropolyacids.

Exemplified as the organometallic complex catalysts are $Al_2(C_2H_5)_3Cl_3$-$TiCl_4$, $Al_2(C_2H_5)_3Cl_3$-$VOCl_3$, $AlC_2H_5Cl_2$-$\pi$-$C_3H_5NiBr$, $Al_2(C_2H_5)_3$-$Cl_3$-$Ni(C_5H_7O_2)_2$, $Al(C_2H_5)_2Cl$-$Cr(C_5H_7O_2)_3$, and $Cl_2Pd(PhCN)_2$.

The oligomerization can be done under the conditions of temperatures from 0° to 300° C., pressures form the atmospheric pressure to 30 Kg/cm$^2$, and reaction times from 1 to 30 hours. These conditions may be selected according to the kind of olefin starting material and a catalyst employed.

Any type of treatment system such as batchwise, semi-batchwise or continuous operation can be adopted. In the case of continuous operation, LHSV (liquid hourly space velocity) is preferably in the range of 0.1 to 20.

When olefins are treated in the presence of the foregoing catalysts, either only olefins or olefins together with an inert solvent can be treated.

When olefin starting material is oligomerized by the above catalyst, oligomers having 14 to 36 carbon atoms are obtained, while heavier components are sometimes produced. In that case, in order to eliminate substantially the heavier components, the branched internal olefins of this invention must be separated from the heavier components by distillation.

Especially preferable range of the number of carbon atoms of oligomers as the material for paper sizing composition is 16 to 28, and it is desirable that the oligomers consists of dimers of olefin starting materials or contain mainly the dimers.

The reaction products obtained from oligomers having less than 14 carbon atoms and maleic anhydride cannot produce satisfactory sizing effect and its storage stability is not good enough. With regard to the reaction product obtained from oligomers having more than 36 carbon atoms, the viscosity of the reaction product is too high, which is undesirable for practical uses because the handling of the reaction product is not easy.

The straight chain internal olefins of (B) component in the present invention can be any of those having 14 to 36 carbon atoms, preferably 15 to 24 carbon atoms, comprising more than 90 mole percent of the olefins which have a double bond at 2nd position or higher positions, and having no branched carbon chain.

These are exemplified by n-pentadecene-2, n-pentadecene-3, n-pentadecene-6, n-hexadecene-4, n-hexadecene-5, n-hexadecene-8, n-heptadecene-3, n-heptadecene-5, n-heptadecene-7, n-octadecene-3, n-octadecene-4, n-octadecene-9, n-nonadecene-2, n-nonadecene-7, n-eicosene-4, n-eicosene-10, n-heneicosene-3, n-heneicosene-9, n-tetracosene-2, n-tetracosene-5 and n-tetracosene-11.

These olefins can be used singly or in a mixture of two or more kinds. From economical viewpoint, mixed olefins of two or more kinds are preferably used.

The olefins which are industrially available are: straight chain internal olefins each having a double bonds in the middle portion of molecular chain (mainly at 6th or higher position) which olefins are obtained by disproportionation of lower olefins; straight chain internal olefins in which double bonds are distributed almost evenly in molecular chains and which are obtained by dehydrogenation of straight chain paraffins that have the same number of carbon atoms as that of the straight chain internal olefins; and a mixture of straight chain internal olefins in which double bonds exist densely at 2nd, 3rd and 4th positions and which are prepared by isomerizing straight chain $\alpha$-olefins having the same number of carbon atoms as those of the straight chain internal olefins with a catalyst such as an acid. Especially preferable one is a mixture of straight chain internal olefins which mixture comprises 10 to 65 mole percent, respectively, of olefins each having a double bond at 2nd, 3rd or 4th position and the sum of these olefins is not less than 70 mole percent.

The reaction product of straight chain internal olefins having less than 14 carbon atoms with maleic anhydride cannot produce satisfactory sizing effect and its dispersion stability is not good. When the number of carbon atoms exceeds 36, the viscosity of reaction product is too high which is undesirable for practical uses.

The addition reaction between maleic anhydride and the thus prepared branched internal olefins or the straight chain internal olefins, is carried out in accordance with the conventional method. That is, both the materials are heated in an inert gas atmosphere such as nitrogen gas at a temperature of 180° to 250° C. and at the atmospheric pressure or at an elevated pressure. This reaction proceeds easily. The molar ratio of both the materials is not restricted, however, 0.2 to 2 moles of maleic anhydride is generally used to 1 mole of the olefin. After the reaction, alkenyl succinic anhydride as the reaction product is obtained by removing unreacted maleic anhydride and unreacted olefin by means of reduced pressure distillation. In this reaction, it is also possible that the branched internal olefin and the straight chain internal olefin are mixed so as to produce a reaction product containing certain ratios of (A) component and (B) component and the mixed olefin is then caused to react with maleic anhydride.

In this addition reaction, the main reaction product is an adduct of 1 mole of olefin with 1 mole of maleic anhydride. However, small quantities of by-products such as an adduct of 1 mole of olefin with 2 moles of maleic anhydride, 1:2-adduct; and polymer of maleic anhydride are produced. These by-products may be either removed or not removed. From economical viewpoint, it is desirable to use the reaction product without removing the by-products. The reaction product is further subjected to ordinary hydrogenation reaction with using a solid catalyst such as palladium or Raney nickel to obtain alkyl succinic anhydride, which comes also within the scope of the present invention.

The compounding ratios of the thus obtained (A) component and (B) component are 20 to 90% by weight of (A) component and 10 to 80% by weight of (B) component, and preferably 30 to 80% by weight of (A) component and 20 to 70% by weight of (B) component. When (A) component is less than 20% by weight, the sizing effect and stability of water dispersion are not suffice. While, if (A) component exceeds 90% by weight, the sizing effect is also not good. Therefore, both the outer ranges are not desirable.

With the composition of (A) component and (B) component in the above-defined ratios, the sizing effect and stability of water dispersion become excellent owing to the synergistic effect of both components (A) and (B), which fact has never been expected even by those skilled in the art.

When paper pulp is sized by using the sizing composition obtained in the above-described process, the composition is homogeneously dispersed in water by a forced mixing apparatus such as a homogeneous mixer, homogenizer or high pressure emulsifier and the obtained dispersion is then added to pulp slurry.

When the sizing composition is dispersed in water, a protective colloid such as cationized starch, gelatin, polyvinyl alcohol, cationic polyacrylamide, or polyethylene imine, or a nonionic emulsifier can be used together. Among the above dispersing agents, the cationized starch, cationic polyacrylamide and polyethylene imine have also the effect as fixing agents to pulp.

The nonionic emulsifiers are exemplified by polyoxyalkylene sorbitan fatty acid ester such as polyoxyethylene sorbitan trioleate; polyoxyalkylene sorbitol fatty acid esters such as polyoxyethylene sorbitol hexaoleate, polyethylene sorbitol laurate and polyoxyethylene sorbitol oleate laurate; polyoxyalkylene alkyl ether such as polyoxyethylene alkyl ether; polyoxyalkylene alkylaryl ether such as polyoxyethylene alkylphenol; polyoxyalkylene monoester such as polyoxyethylene alkyl monoester; and their acetylated products; polyoxyalkylene diester such as polyoxyethylene alkyl diester; polyoxyalkylene alkylamine such as polyoxyethylene alkylamine; polyoxyalkylene alkylamide such as polyoxyethylene alkylamide; ester of polyalcohol with fatty acid; and higher alcohol.

In the present invention, the quantity of the foregoing protective colloid used together with the paper sizing composition, is determined according to the dispersibility of the composition in water and the fixing property to pulp of prepared paper sizing medium. The quantity of the protective colloid is generally in the range of 50 to 500%, preferably 100 to 200%, relative to the paper sizing composition.

The quantity of nonionic emulsifier is determined according to the dispersibility of paper sizing composition, and is generally in the range of 3 to 30%, preferably 5 to 20% relative to the paper sizing composition.

In the case that the above nonionic emulsifier is previously mixed into the paper sizing composition of the present invention and the mixture is then dispersed in water, any forced mixing apparatus is not necessary, which apparatus is necessary when dispersing is done using a protective colloid. The sizing composition with nonionic emulsifier can be easily dispersed only by using a pulp-mixing aspirator or by passing the mixture through an orifice (these methods are hereinafter referred to as "self-emulsifying method"). Therefore the paper making process can be simplified.

The quantity of paper sizing composition used in the present invention varies to some extent according to the kind and usages of paper to be produced. The quantity of the paper sizing composition is, however, generally in the range of 0.05 to 5.0% by weight to dry-basis pulp. It is possible to add more than 5.0% by weight of paper sizing composition but the increase of sizing effect can hardly be expected so that the addition of more than 5% is not advantageous in economical viewpoint.

As described above, when the paper sizing composition of this invention is used together with a cationic protective colloid or a nonionic emulsifying agent in neutral or alkaline conditions, the sizing composition can be dispersed well in water. Owing to the use of specific composition of components (A) and (B), the sizing composition produces excellent sizing effect, that is, desired sizing effect can be obtained by using smaller quantity of the sizing composition as compared with the conventional art. Furthermore, it maintains good sizing effect during long term preservation, that is, the sizing effect of prepared sizing medium after long term preservation is almost the same as the effect produced just after it is made up. This fact is more advantageous as compared with conventional sizing agents.

The paper sizing composition of this invention can be used of course singly, and if desired, it can be used together with known sizing agents by mixing with them in any mixing ratio.

It should be noted also that known pigments and fillers such as clay, talc, titanium oxide, calcium carbonate, calcium sulfate and diatomaceous earth can be used in paper making process together with the sizing composition of the present invention.

The preparation and uses of the sizing composition of the invention will be described in more detail in the following examples. It should be noted, however, that the present invention be limited not by the specific disclosure herein but only by the appended claims.

PREPARATION EXAMPLE A-1

A 1 liter glass-made reaction vessel equipped with a stirrer, thermometer and cooling pipe, was fed with 500 ml of n-octene-1 and 50 g of Nafion 511 (trademark of cation exchange resin containing fluorosulfonic radical, made by E. I. du Pont de Nemours). Reaction was carried out for 1 hour at 120° to 140° C. After the reaction, Nafion 511 was separated from the reaction mixture by filtration and the reaction mixture was treated by an adsorbent, Kyowaad 500 (trademark, made by Kyowa Chemical Industry Co., Ltd.; $Mg_6Al_2(OH)_{16}CO_3.4H_2O$) to eliminate the free acid derived from the catalyst. After that, by reduced pressure distillation, 225 g of branched internal olefin having 16 or more carbon atoms was obtained. The distribution of carbon atom number was $C_{16}$: 89% and $C_{24}$: 11%.

A stainless steel autoclave equipped with a stirrer and a thermometer was fed with 150 g of the branched internal olefin and 65 g of maleic anhydride. The air in the reaction system was completely replaced by dry nitrogen gas and reaction was carried out for 4 hours at 210°0 C.

The reaction mixture was then subjected to reduced pressure distillation to remove unreacted olefin and maleic anhydride and 101 g of maleic modified reaction product (A-1) was obtained.

PREPARATION EXAMPLE A-2

A 1 liter glass-made reaction vessel equipped with a stirrer, thermometer and cooling pipe, was fed with 500 ml of n-dodecene-1 and 50 g of synthetic silica-alumina and the contents were allowed to react for 1 hour at 150° to 180° C. After the reaction, the catalyst was removed from the reaction mixture by filtration. By reduced pressure distillation, 163 g of dimer as the branched internal olefin was obtained from the reaction mixture. Then, a stainless-steel autoclave equipped with a stirrer and thermometer was fed with 140 g of the branched internal olefin and 40.8 g of maleic anhydride. The air in the reaction system was completely replaced by dry nitrogen gas and reaction was carried out for 4 hours at 210° C. The reaction mixture was then subjected to reduced pressure distillation to remove unreacted olefin and maleic anhydride, and 38 g of maleic modified reaction product (A-2) was obtained.

PREPARATION EXAMPLE B-1

A mixture of n-paraffins of 15 to 18 in carbon atom number together with hydrogen gas was subjected to dehydrogenation by feeding them into a stainless steel-made reaction vessel containing 30 ml of catalyst, $Pt.Li_2O.Al_2O_3$. The conditions of reaction were: reaction temperature: 470° C., feeding rate: 15 ml/min. and molar ratio of $H_2$/n-paraffin: 8.0. The olefin content of the effluent from the outlet of reaction vessel was about 12%. A mixture of straight chain internal olefins of 15 to 18 in carbon atom number ($C_{15}$: 5 wt %, $C_{16}$: 37 wt %, $C_{17}$: 38 wt %, $C_{18}$: 20 wt %) was obtained by passing the reaction mixture through a molecular sieve. According to $^{13}$C-NMR analysis, the positions of double bonds were 3 mole percent of 1st position, 16 mole percent of 2nd position, 22 mole percent of 3rd position, 24 mole percent of 4th position, and 35 mole percent of 5th and higher positions.

Under the same conditions as those of Preparation Example A-1, 240 g of the mixture of straight chain internal olefins was reacted with 95 g of maleic anhydride to obtain 220 g of maleic modified reaction product (B-1).

PREPARATION EXAMPLE B-2

A stainless steel-made continuous reaction tube was fed with 100 ml of 12-tungstosilicic acid carried on silica gel and the reaction tube was maintained at 100° C. α-Olefin of 16 to 18 in carbon atom number ($C_{16}$: 56 wt %, $C_{18}$: 44 wt %, obtained by Ziegler process) was fed to this reaction tube at a flow rate of 300 ml/hour. According to $^{13}$C-NMR analysis, the positions of double bonds of the effluent of the reaction tube were 2 mole percent of 1st position, 40 mole percent of 2nd position, 28 mole percent of 3rd position, 15 mole percent of 4th position, and 15 mole percent of 5th and higher positions. Under the same conditions as those of Preparation Example A-1, 480 g of the thus obtained straight chain internal olefins were reacted with 195 g of maleic anhydride to obtain 404 g of maleic modified reaction product (B-2).

PREPARATION EXAMPLE B-3

Under the same conditions as those of Preparation Example A-1, 300 g of n-octadecene-9 was reacted with 115 g of maleic anhydride to obtain 248 g of maleic modified reaction product (B-3).

USE EXAMPLE 1

The maleic modified reaction products that were obtained in the above Preparation Examples were mixed together according to the mixing ratios shown in the following Table 1. Each 1 g of the thus prepared sizing composition was mixed with 20 g of 10 wt % cationized starch aqueous solution and 79 g of water and the mixture was emulsified by a homogenizer to obtain an aqueous dispersion.

The stability of these aqueous dispersions was observed. Furthermore, sizing degree test was carried out with the following paper making method. The results of these tests are shown in the following Table 1. For comparison, the results of sole maleic modified reaction products are also shown in the same table.

(Paper Making Method)

To 1% pulp slurry (L-BKP 450 ml c.s.f.) was added 20% by weight (to dry pulp) of $CaCO_3$ as a filler. 0.1 wt % (to dry pulp) of sizing composition was added in the form of an aqueous solution. Sizing treatment was done by stirring and dispersing the mixture. Paper of 60 g/m² in basis weight was then made using TAPPI standard machine. After that, the wet paper was dehydrated by a press for 5 minutes, which was followed by drying at 100° C. for 1 minute. The moisture of the paper was then adjusted by placing it in an atmosphere of 65% relative humidity for 24 hours. The properties of paper were then determined by Stöchigt method.

TABLE 1

| No. | Sizing Composition Component | Ratio (wt %) | Stability of Aqueous Soln. (After 24 hrs.) | Sizing Degree (sec.) Just after Emulsifying | 24 hrs. after Emulsifying |
|---|---|---|---|---|---|
| 1 | A-1 | 70 | Stable | 18 | 8 |
|   | B-1 | 30 |  |  |  |
| 2 | A-1 | 40 | " | 14 | 6 |
|   | B-1 | 60 |  |  |  |
| 3 | A-1 | 70 | " | 20 | 10 |
|   | B-2 | 30 |  |  |  |
| 4 | A-1 | 35 | " | 14 | 7 |
|   | B-2 | 65 |  |  |  |
| 5 | A-1 | 50 | " | 16 | 7 |
|   | B-3 | 50 |  |  |  |
| 6 | A-2 | 75 | " | 19 | 8 |
|   | B-1 | 25 |  |  |  |
| 7 | A-2 | 75 | " | 21 | 10 |
|   | B-2 | 25 |  |  |  |
| 8 | A-2 | 80 | " | 19 | 8 |
|   | B-3 | 20 |  |  |  |
| 9 | A-2 | 35 | " | 14 | 6 |
|   | B-3 | 65 |  |  |  |
| 10 | A-1 | 100 | " | 6 | 3 |
| 11 | A-2 | 100 | " | 9 | 4 |
| 12 | B-1 | 100 | Separated to 2 layers | 0 | 0 |
| 13 | B-2 | 100 | Like Pudding | 4 | 1 |
| 14 | B-3 | 100 | " | 0 | 0 |

USE EXAMPLE 2

The maleic modified reaction products that were obtained in the above Preparation Examples were mixed together according to the present invention. Each 10 g of the thus prepared sizing composition was mixed with 1 g of emulsifier: polyethylene glycol nonylphenyl ether (trademark: Nonipol 160, made by Sanyo Chemical Industries, Ltd.) and they were well stirred together. 99 g of water was added to 1 g of this mixture and it was emulsified by stirring for 1 minute with a propeller agitator to obtain a sizing medium.

A fixing agent of 0.3 wt % (to dry pulp) of polyamide polyamine resin was added to 1% slurry of pulp and the above sizing medium was then added to this mixture (0.5 wt % of sizing composition to dry pulp).

In the like manner as Use Example 1, sizing degrees were determined. Furthermore, the prepared sizing mediums were left to stand still for 5 hours and sizing degrees were also determined. The results of these tests are shown in the following Table 2. For comparison, the results of sole maleic modified reaction products are also shown in the same table.

TABLE 2

| | Sizing Composition | | Sizing Degree (sec.) | |
|---|---|---|---|---|
| No. | Component | Ratio (wt %) | Just after Emulsifying | 5 hrs. after Emulsifying |
| 1 | A-1 | 50 | 29 | 22 |
| | B-1 | 50 | | |
| 2 | A-1 | 40 | 29 | 22 |
| | B-2 | 60 | | |
| 3 | A-1 | 80 | 30 | 22 |
| | B-3 | 20 | | |
| 4 | A-1 | 35 | 28 | 22 |
| | B-3 | 65 | | |
| 5 | A-2 | 50 | 29 | 22 |
| | B-1 | 50 | | |
| 6 | A-2 | 75 | 32 | 25 |
| | B-2 | 25 | | |
| 7 | A-2 | 30 | 28 | 22 |
| | B-2 | 70 | | |
| 8 | A-2 | 70 | 30 | 23 |
| | B-3 | 30 | | |
| 9 | A-1 | 100 | 26 | 20 |
| 10 | B-1 | 100 | 22 | 4 |
| 11 | B-3 | 100 | 22 | 0 |

What is claimed is:

1. A paper sizing composition which comprises:
   20 to 90% by weight of (A) a reaction production and/or its hydrogenation product which reaction product is obtained by reacting maleic anhydride to branched internal mono-olefins having 16 to 28 carbon atoms which are obtained by oligomerizing one or a mixture of straight chain mono-olefin starting materials having 6 to 18 carbon atoms and
   10 to 80% by weight of (B) another reaction product and/or its hydrogenation product which reaction product is obtained by reacting maleic anhydride with straight chain internal mono-olefins having 15 to 24 carbon atoms.

2. The paper sizing composition in claim 1, wherein the number of carbon atoms of said olefin starting materials of said (A) component is 8 to 12.

3. The paper sizing composition in claim 1, wherein said olefin starting materials of said (A) component are straight chain α-olefins.

4. The paper sizing composition in claim 1, wherein said olefin starting materials of said (A) component are straight chain internal olefins.

5. The paper sizing composition in claim 1, wherein straight chain internal mono-olefins of said (B) component comprise 10 to 65 mole percent, respectively, of mono-olefins each having a double bond at 2nd, 3rd or 4th position and the sum of said olefins is not less than 70 mole percent.

6. The paper sizing composition in claim 1 wherein said straight chain internal mono-olefins of said (B) component comprise a mixture of mono-olefin in which the double bonds are almost evenly distributed at every position in their molecular chains.

7. The paper sizing composition in claim 1, wherein said straight chain internal mono-olefins of said (B) component comprise mono-olefins in which the double bonds are densely distributed in the middle portions of their molecular chains.

8. The paper sizing composition in claim 5, wherein said mixture of straight chain internal mono-olefins is obtained by isomerizing straight chain α-olefins having the same number of carbon atoms as said internal mono-olefins using an acid catalyst.

9. The paper sizing composition in claim 1, wherein said composition contains a dispersing agent.

10. The paper sizing composition in claim 9, wherein said dispersing agent is at least one member selected from the group consisting of cationized starch, gelatin, polyvinyl alcohol, cationic polyacrylamide and polyethylene imine.

11. The paper sizing composition in claim 1, wherein said composition contains an emulsifying agent.

12. The paper sizing composition in claim 11, wherein said emulsifying agent is at least one member selected from the group consisting of polyoxyalkylene sorbitol fatty acid ester, polyoxyalkylene sorbitan fatty acid ester, polyoxyalkylene alkyl ether, polyoxyalkylene alkylaryl ether, polyoxyalkylene monoester, and their acetylated products, and polyoxyalkylene diester.

* * * * *